United States Patent [19]

Calvert et al.

[11] Patent Number: 5,500,315
[45] Date of Patent: Mar. 19, 1996

[54] PROCESSES AND COMPOSITIONS FOR ELECTROLESS METALLIZATION

[75] Inventors: Jeffrey M. Calvert, Burke, Va.; Walter J. Dressick, Fort Washington, Md.; Gary S. Calabrese, North Andover; Michael Gulla, Millis, both of Mass.

[73] Assignee: Rohm & Haas Company, Philadelphia, Pa.

[21] Appl. No.: 317,347

[22] Filed: Oct. 4, 1994

Related U.S. Application Data

[63] Continuation of Ser. No. 62,706, May 17, 1993, Pat. No. 5,389,496, which is a continuation-in-part of Ser. No. 691,565, Apr. 25, 1991, abandoned, which is a continuation-in-part of Ser. No. 22,439, Mar. 6, 1987, Pat. No. 5,077,085, and Ser. No. 182,123, Apr. 14, 1988, Pat. No. 5,079,600.

[51] Int. Cl.$^6$ .............................. G03C 5/58; G03F 7/038
[52] U.S. Cl. .............................. 430/16; 430/17; 430/315; 430/324; 427/98; 427/301; 427/304; 427/306; 428/209; 428/420
[58] Field of Search .............................. 430/311, 16, 17, 430/231, 315, 324; 428/420, 209; 427/98, 304, 301, 306

[56] References Cited

U.S. PATENT DOCUMENTS

| 3,671,250 | 6/1972 | Andrews et al. | 96/88 |
|---|---|---|---|
| 3,853,589 | 12/1974 | Andrews et al. | 117/47 A |
| 4,426,247 | 1/1984 | Tamamura et al. | 156/643 |
| 4,604,699 | 8/1986 | DeLuca et al. | 427/98 |
| 4,661,384 | 4/1987 | Sirinyan et al. | 427/304 |
| 4,666,735 | 5/1987 | Hoover et al. | 427/43.1 |
| 4,738,869 | 4/1988 | Baumgartner | 427/54.1 |
| 4,746,536 | 5/1988 | Ichikawa et al. | 427/54.1 |
| 4,976,990 | 12/1990 | Bach et al. | 427/98 |
| 4,981,715 | 1/1991 | Hirsch et al. | 427/53.1 |
| 4,996,075 | 2/1991 | Ogawa et al. | 427/12 |
| 5,045,436 | 9/1991 | Tieke et al. | 430/315 |
| 5,077,085 | 12/1991 | Schnur et al. | 427/98 |
| 5,079,600 | 1/1992 | Schnur et al. | 427/98 |

FOREIGN PATENT DOCUMENTS 1463803  2/1977  United Kingdom.

*Primary Examiner*—Richard L. Schilling
*Attorney, Agent, or Firm*—Robert L. Goldberg

[57] ABSTRACT

Methods and compositions for electroless metallization. In one aspect, the invention is characterized by the use of chemical groups capable of ligating with an electroless metallization catalyst, including use of ligating groups that are chemically bound to the substrate. In a preferred aspect, the invention provides a means for selective metallization without the use of a conventional photoresist patterning sequence, enabling fabrication of high resolution metal patterns in a direct and convenient manner.

5 Claims, No Drawings

5,500,315

PROCESSES AND COMPOSITIONS FOR ELECTROLESS METALLIZATION

CROSS REFERENCE TO RELATED APPLICATIONS

This is a continuation of application(s) Ser. No. 08/062, 706 filed on May 17, 1993 now U.S. Pat. No. 5,389,496, which is a continuation-in-part of prior applications Ser. No. 07/691,565, filed Apr. 25, 191, now abandoned, which is a continuation-in-part of Ser. No. 07/022,439, filed Mar. 6, 1987 now U.S. Pat. No. 5,077,085 and Ser. No. 07/182,123, filed Apr. 14, 1988 now U.S. Pat. No. 5,079,600.

BACKGROUND OF THE INVENTION

1. Field of the Invention

The present invention relates to processes and compositions for electroless metallization and related articles of manufacture and, more particularly, the invention relates to the use of substrate chemical groups capable of ligating with a variety of electroless metallization catalysts, including tin-free catalysts, and selective electroless plating through the use of such ligating groups.

2. Background Art

Electroless metallization procedures typically require multiple and complex processing steps. See, for example, reviews of electroless plating in C. R. Shipley, Jr., *Plating and Surface Finishing*, vol. 71, pp. 92–99 (1984); and *Metal Finishing Guidebook and Directory*, vol. 86, published by Metals and Plastics Publications, Inc. (1988), both incorporated herein by reference. One typical procedure for metallization of polymeric substrates employs a colloidal palladium-tin catalyst in the following sequence: (1) pre-cleaning the substrate surface; (2) microetching, for example with a chromic-based solution; (3) conditioning the etched substrate surface; (4) adsorption of the palladium-tin catalyst onto the conditioned surface; (5) treatment with an accelerator to modify and activate the absorbed catalyst; and (6) treatment with an electroless plating solution. See, for example, U.S. Pat. Nos. 4,061,588 and 3,011,920. A number of fundamental studies have been performed on this and related electroless procedures. See, for example, J. Horkans, *J. Electrochem. Soc.*, 130, 311 (1983); T. Osaka, et al., *J. Electrochem. Soc.*, 127, 1021 (1980); R. Cohen, et al., *J. Electrochem. Soc.*, 120, 502 (1973); and N. Feldstein, et al., *J. Electrochem. Soc.*, 119, 668 and 1486 (1972).

While the exact composition and structure of such a Pd/Sn catalyst have not been confirmed, and the detailed mechanism by which a Pd/Sn colloid adheres to a substrate is not fully understood, the following is known and/or currently postulated. A palladium-tin electroless catalyst typically is generated by mixing multi-molar stannous chloride and a palladium chloride in an acidic aqueous solution containing excess chloride ion. Sn(II) reduces the Pd(II) species, likely via an inner-sphere redox reaction in a Pd/Sn complex, resulting in a colloidal suspension with a dense metallic core within a less dense tin polymer layer. The central portion of the colloid is composed of an intermetallic compound of stoichiometry reported to be $Pd_3Sn$. This inner core is believed to be a cluster containing up to 20 atoms with palladium principally in the zero and +1 oxidation states. This inner core is the actual catalyst in the initial metal reduction that leads to electroless metal deposition.

Surrounding this core is a layer of hydrolyzed stannous and stannic species that forms an outer shell of oxy- and/or hydroxy-bridged oligomers and polymers together with associated chloride ions. This layer is known as beta-stannic acid. The composition of the colloidal suspension contains a high concentration (multi-molar excess) of stannous ions relative to Pd which continue to hydrolyze and form higher oligomers on the outer surface of the initially formed colloidal particles. Consequently the thickness and degree of polymerization of the outer tin shell changes over time. The resultant colloidal particle has a net negative charge.

Adhesive properties of the outerpolymeric outer shell attach the catalyst to the substrate to be plated, known in the art as the activation process. The negative charge of the outer tin shell prevents aggregation of the colloids permitting individual attachment to the substrate. The reducing power of the Sn(II) acts as an anti-oxidant and protective layer that maintains the catalytic core in the low valent Pd state necessary to initiate plating. Activation is followed by an acceleration step whereby the catalyst core is exposed. Acceleration can be achieved by a variety of means, for instance by "subtractive" type means of dissolving the stannous protective layer at high chloride ion concentrations to form soluble $SnCl_4^{2-}$, or by oxidizing the shell to the more soluble Sn(IV) by exposure to oxygen from the ambient. "Additive" type acceleration sequences are also known. For example, European Patent Application 90105228.2 discloses the application of an acidic solution of $PdCl_2$ to the intact adsorbed colloid. The stannous polymer layer of the particle reduces the palladium ion in situ to form a metallic Pd deposit on which plating can occur. After activation, the substrate is immersed in an electroless plating solution. A typical electroless metal plating solution comprises a soluble ion of the metal to be deposited, a reducing agent and such other ligands, salts and additives that are required to obtain a stable bath having the desired plating rate, deposit morphology and other characteristics. Common reductants include hypophosphite ion ($H_2PO_2^-$), formaldehyde, hydrazine or dimethylamine-borane. The reductant reacts irreversibly at the catalyst core to produce an active hydrogen species, presumably a palladium hydride. The surface hydrogen is also a potent reductant which transfers electrons to the soluble metal complex in the bath and produces a metal deposit on top of the catalyst, which eventually covers the core sufficiently to block access to the external solution. For certain deposits, such as copper, nickel and cobalt, the nascent layer can itself become "charged" with hydrogen and continue to reduce metal ion to metal, leading to "autocatalytic" build-up of an electroless deposit onto the activated surface. In a competitive reaction, surface hydrogen atoms combine to evolve $H_2$ gas. This latter reaction has never been completely suppressed. Therefore, not all available reducing equivalents in the electroless bath can be used for metal deposition. For a properly catalyzed surface, the choice of electroless metal plating solution is determined by the desired properties of the deposit, such as conductivity, magnetic properties, ductility, grain size and structure, and corrosion resistance.

Such a palladium-tin catalyst system presents a number of limitations. At a minimum three steps are required—activation, acceleration and plating. Often substrate pre-treatment and other additional steps are necessary to provide uniform plating. The colloidal catalyst also is readily oxidized and stannous ions must be replenished by regular addition of Sn(II) salts. Further, the colloid size may fix packing density thereby making difficult uniform plating of ultra-small objects, e.g. objects less than about 1,000 angstroms in size. Subtractive-type acceleration requires a precise and often difficult balance of exposing the palladium core without dissolving the portion of the stannous shell that provides adherence to the substrate surface. Further, substrate adhesion of a Pd/Sn catalyst has been found to be a relatively non-specific phenomenon. For example, the catalyst will only weakly adhere to a smooth photoresist coating, requiring a pre-etch step to provide a more textured surface and thereby increasing processing time and costs. For many situations, such as high resolution lithography, such pre-etching is not feasible. Further, a number of materials are "colloidophobic", i.e. materials to which a Pd/Sn catalyst does not adsorb. These materials include silica, certain metals and some plastics.

Recently, several electroless plating procedures have been reported, the procedures generally employing a palladium catalyst and a polyacrylic acid or polyacrylamide substrate coating. See, U.S. Pat. Nos. 4,981,715 and 4,701,351; and Jackson, *J. Electrochem. Soc.*, 135, 3172–3173 (1988), all incorporated herein by reference.

A common method for producing a patterned metallized image includes use of a photoresist coating. In an additive metallization approach, photoresist is applied to a substrate surface; the resist is exposed to provide selectively soluble portions of the photoresist coating; a developer is applied to bare selected portions of the substrate surface; those selected portions are metallized; and the remaining resist stripped from the substrate surface. See, generally, Coombs, *Printed Circuits Handbook*, ch. 11 (McGraw Hill 1988), incorporated herein by reference. A print and etch procedure is a subtractive approach where in the case of circuit line fabrication, a copper layer is selectively chemically etched through use of a photoresist to define the circuit traces. For higher performance applications, it is crucial that circuit sidewalls be uniform and essentially vertical. Resolution limits exist with a print and etch sequence, however, which are inherent in the subtractive nature of this approach.

SUMMARY OF THE INVENTION

The present invention comprises an electroless metal plating-catalyst system that overcomes many of the limitations of prior systems. In one aspect of the invention, a process is provided comprising steps of providing a substrate comprising one or more chemical groups capable of ligating to an electroless plating catalyst, at least a portion of the chemical groups being chemically bonded to the substrate; contacting the substrate with the electroless metal plating catalyst; and contacting the substrate with an electroless metal plating solution to form a metal deposit on the substrate. The chemical groups can be, for example, covalently bonded to the substrate.

In another preferred aspect, the invention provides a process for selective electroless metallization, comprising steps of selectively modifying the reactivity of a substrate to an electroless metallization catalyst; contacting the substrate with the electroless metallization catalyst; and contacting the substrate with an electroless metallization solution to form a selective electroless deposit on the substrate. The substrate reactivity can be modified by selective treatment of catalyst ligating groups or precursors thereof on the substrate, for example by isomerization, photocleavage or other transformation of the ligating or precursor groups. Such direct modification enables selective plating in a much more direct and convenient manner than prior selective plating techniques. Specifically, the present invention provides selective electroless plating without the use of a photoresist or an adsorption type tin-containing plating catalyst.

The one or more chemical groups capable of binding to the electroless catalyst may be provided by a variety of means. The material of construction of the substrate may comprise the catalyst ligating groups, for example a polyvinylpyridine substrate or an alumina substrate. Substrates that do not inherently comprise such ligating groups may be treated to provide the groups. For example, a source of the ligating groups may be formulated as a material of construction of the substrate. Alternatively, a substrate may comprise suitable precursor groups which upon appropriate treatment provide the necessary catalyst ligating groups. Such treatment will vary with the particular ligating group and includes, for example, thermolysis, treatment with chemical reagents, photochemical modification such as isomerization or photocleavage of a precursor group, and plasma etching. Further, such treatment methods can provide precursor groups, such as hydroxyl, carboxyl, amino and others to which a ligating group can be bonded. Still further, the ligating chemical groups or precursors thereof may be provided by contacting at least portions of the substrate surface with a compound or composition comprising the ligating groups, the ligating groups preferably adhering well to the substrate surface, for instance by chemical and/or physical interaction. If chemical bond formation is employed as the substrate adherence means, substrate adhesion and catalyst ligation functions may be performed by application of a single molecule or, alternatively, by application of multiple molecules with subsequent linkage therebetween.

A variety of metallization catalysts may be employed, including tin-free catalysts, with palladium (II) compounds and compositions preferred for the generally superior catalytic activity those catalysts provide. A substrate is preferably treated with a solution of the metallization catalyst, for example an aqueous solution or a solution of an organic solvent. The catalyst solution preferably comprises other materials such as ancillary ligands, salts and buffers to enhance the stability of the catalyst solution and thereby to provide suitable catalyst activity as well as convenient use and storage of the solution.

The substrate to be electrolessly plated according to the present invention may be a variety of materials such as a conductive material, a semiconductor material, an electrically nonconductive material, and more specifically, electronic packaging substrates such as a printed circuit board or a precursor thereof. In a preferred aspect, the invention is employed to metallize lipid tubule microstructures. It is believed that a wide variety of metals may be electrolessly plated in accordance with the present invention, for example cobalt, nickel, copper, gold, palladium and various alloys.

As is apparent to those skilled in the art, notable advantages of the invention include an electroless catalyst system that requires fewer and simpler processing steps in comparison to current Pd/Sn colloid catalyst adsorption based systems; use of more stable and convenient catalysts, including tin-free catalysts; and improved catalyst adhesion to a substrate allowing plating of more dense initiation and of greater uniformity and selectivity. The invention also provides selective patterning of substrate ligating groups, thereby enabling a selective metal deposit without the use of a conventional photoresist patterning sequence.

The terms-"ligate" or "ligating" or "ligation", as used herein in reference to the interaction between an electroless metallization catalyst and the substrate chemical groups of the invention, refers to any attraction, binding, complexing, chelating or sequestering, whatever the nature or extent of such attraction, binding, complexing, chelating or sequestering, between the catalyst and the substrate chemical group.

DESCRIPTION OF THE PREFERRED EMBODIMENTS

Many substrates or substrate surfaces capable of being plated according to the present invention intrinsically contain chemical groups, or appropriate precursors of chemical groups, that are able to ligate an electroless plating catalyst. For example, a polyvinylpyridine film intrinsically contains such chemical groups with the pendant pyridine serving as the catalyst ligating group. As discussed herein, the pyridyl group has been found to be a particularly preferred ligating group for a palladium catalyst. For a discussion of the pyridyl moiety as a ligating group, see Calvert, et al., *Inorganic Chemistry*, 21, 3978 (1982), incorporated herein by reference. Similarly, a substrate comprising aluminum oxide will bind a palladium catalyst by the AlO and AlOH groups of the alumina. Further, the ligating material need not be the sole component of the substrate. Thus, the ligating material may be physically blended as one of multiple components comprising the substrate if sufficient ligating moieties are accessible at the substrate surface to ligate to the catalyst.

A possible shortcoming of such a blending approach is that incorporation of large quantities of a second material may impair the film-forming or other properties of the bulk material. A potential solution to this problem is to incorporate a surfactant form of the ligating component into the bulk material by proper choice of the relative solubility/polarity characteristics of the ligating component and the surfactant. By incorporating a small percentage of the surfactant into the bulk, a high surface concentration of the ligating component could be produced. An analogous approach has been employed in the photoresist arts, where a small quantity of surfactant is formulated into the resist to enhance film planarity by reducing the surface tension through a high surface concentration of surfactant.

Many substrates that do not inherently comprise suitable ligating groups may be readily modified to possess the necessary ligating groups. Substrate modification methods include, but are not limited to, thermolysis, reaction of the surface with one or more chemical reagents, irradiation with photons or ions, vapor phase modification, graft polymerization, x-ray and nuclear radiation treatment or, more generally, any treatment that effects the desired conversion of the substrate. One potential modification sequence provides hydrolysis of a polyimide surface and reacting the hydrolyzed surface with a silane reagent possessing a suitable ligating group, such as β-trimethoxysilylethyl-2-pyridine. Another method provides chemically etching a polyethylene surface with a $Cr_2O_7^{2-}$ solution to provide hydroxyl groups on the substrate surface. The hydroxyl groups should then condense with a suitable compound containing a ligating group, for example nicotinoyl chloride with its pyridyl ligating group. Some of the surface substrate modification methods permit convenient selective treatment of a substrate surface. For example, if a surface can undergo a photochemical conversion to reveal a ligating group, that surface can be exposed to masked radiation and directly produce a pattern of catalyst binding sites. After treatment with a suitable catalyst, the patterned catalyst surface can then be electrolessly metallized to produce a negative tone image of the mask employed.

Rather than directly modifying the substrate, the substrate may be imparted with suitable ligating groups by indirect modification of the surface. For example, a substrate may be coated with one or more film layers, each layer comprising one or more suitable ligating agents. The film layer preferably adheres well to the substrate, for example by containing a functional group that will chemically and/or physically adhere to the substrate.

The adhesive and ligation functions of such a film may be performed by application of a single molecule or, alternatively, by application of multiple molecules with subsequent linkage between each of the molecules. For example, β-trimethoxysilylethyl-2-pyridine provides both ligating and substrate-adherent functionalities. The alkoxysilane group can chemically bind the compound to a substrate. For instance, the trimethoxysilyl group reacts with surface hydroxyl (silanol) functions of a quartz substrate, displacing methanol to directly bond to the substrate. The thus bound pyridyl moiety of the silylpyridyl molecule serves as a ligand for chelating with the plating catalyst.

As noted, the adhesive and ligating functions may be performed by multiple chemical groups with bond formation or other linkage between each of the groups. The linkage connecting the multiple functional groups may be of variable length and chemical composition. Examples include 3-(trimethoxysilyl) propylamine and a quinoline-8-sulfonic acid chloride. The aminosilane is applied as the substrate adsorbent. The coated surface is then reacted with a quinoline-8-sulfonic acid chloride, the $SO_2Cl$ group coupling to the amine group of the coated surface to form a sulfonamide linkage, and the quinolinic group serving as a catalyst ligation moiety. Similarly, 3-(trimethoxysilyl) propylamine can be applied to a substrate and then reacted with the acid chloride group of 4,4'-dicarbonyl chloride-2,2'-bipyridine to form an amide linkage. The pyridyl moieties of this complex serve as catalyst ligating groups. Other silyl amines can be condensed in a similar manner, for example 3-(triethoxysilyl) propylamine. Another sequence provides condensing the hydroxyl groups of a chemically etched polyethylene substrate with a suitable ligating precursor, for example, 3-(trimethoxysilyl)propylamine, which after formation of the oxygen-silyl bond by methanol displacement, the amino group can condense with a suitable ligating compound such as nicotinoyl chloride.

A ligating chemical group comprising a radiation sensitive chromophore can provide selective photochemical patterning and metallization where selective photolysis or radiation ablation modifies the chemical groups on the substrate surface to substantially reduce or eliminate ligating ability in the selected film surface areas. Subsequent exposure to the plating catalyst and metallization solutions provides a positive tone image of the photomask employed. For example, the pyridyl group of β-trimethoxysilylethyl-2-pyridine serves as a chromophore for convenient patterning and subsequent selective metallization of the substrate surface through microlithographic techniques.

Analogously, a ligating film can be employed where selective photolysis transforms a non-ligating group within the film into a ligating group. For example, azoxybenzene derivatives photoisomerize from a weakly or non-ligating azoxybenzene group to the ligating 2-hydroxyazobenzene group. The chelating ability of 2-hydroxyazobenzene and 2-(2-pyridylazo)-1-naphthol has been described in Calabrese, et al., *Inorq. Chem.*, 22, 3076 (1983), incorporated herein by reference. The Photo-Fries reaction is another potential means to provide suitable ligating groups. By this reaction, for example, polyacetoxystyrene can be irradiated with ultraviolet radiation to provide the ligating 2-hydroxyacetophenone moiety.

Depending on the nature of the radiation-sensitive materials employed, such transformations may be accomplished with a variety of exposure sources and imaging tools. For example, ultraviolet or visible light will be suitable for certain transformations, while other transformation may require exposure sources such as electron beam or x-ray treatment. Such energy sources can be provided by image tools known to those in the art, for example ultraviolet contact printers and projection steppers, electron beam writers and x-ray proximity printers.

For such patterning of a ligating film, the film preferably is an ultrathin film, which is a film defined herein to mean a film of a composite thickness of between about ten molecular layers and a single molecular (monomolecular) layer. Such a film can be formed through dip coating or vapor phase deposition procedures as are known in the art. A ligating film composed of multiple layers of ligating groups may not provide highly selective plating. Radiation exposure may fail to penetrate sufficiently the entire thickness of a multiple layer film leaving intact ligating groups in undesired substrate surface areas, thereby resulting in nonselective plating. As irradiation can readily penetrate through the thickness of an ultrathin film, such a film can be patterned with greater precision resulting in greater image resolution.

As described above, the invention provides a substrate surface containing a chemical functional group capable of binding metallization catalysts from solution. One way of binding a catalyst to a surface is by a metal-ligand complexation, or ligation reaction. Though not wishing to be bound by theory, the ability of a substrate ligand L to bind an electroless catalyst, for example a palladium (II) catalyst, should be readily determined by examining the formation equilibrium constant $K_f$ for the generalized complexation reaction (I):

$$Pd^{2+} + L \longleftrightarrow PdL^{2+} \qquad (I)$$

wherein, $K_f$ is equal to the ratio of concentration of products to reactants in reaction (I), i.e., $$K_f = \frac{[PdL^{2+}]}{[Pd^{2+}][L]}$$

Large values of $K_f$ would indicate strong, or essentially irreversible, binding of the catalyst to the ligand. See, generally, A. Martell, et al., "Critical Stability Constants", Plenum Press, New York (1975), where examples of complexation reactions have been tabulated. While little data has been reported for palladium (II) ligation reactions, the general trends for complexation reactions can be obtained by examining the formation constant values for Ni(II). Palladium is directly below nickel in the periodic table and has similar coordination properties. The results with nickel ion shows that through a chelate effect a multidentate ligand (chelate) provides a greater $K_f$ than a corresponding monodentate group, where the term monodentate group refers to a chemical group that can provide only one ligand binding site, and the term multidentate group refers to chemical group or groups that can provide greater than one ligand binding site. For example, chelation of Ni(II) by 2,2'-bipyridine results in a complex that is 10,000 times more stable than a pyridine complex, and 30 times more stable than a bis-pyridine complex. Further, it is believed that a higher $K_f$ provides a metal deposit-with relatively greater adhesion to a substrate upon subsequent metallization.

Thus, a bipyridyl is preferred over a monopyridyl for the relatively stronger bond the bipyridyl forms with an electroless metallization catalyst and the higher quality metal deposit thereby provided. Use of suitable multidentate ligating groups has enabled deposition of thick adherent metal plates, including metal plates of thickness equal to and greater than about 2500 angstroms on smooth, unetched surfaces. In addition to bipyridyl, numerous other multidentate groups should also serve as suitable ligating groups, for example 2,2':6,2"-terpyridine, oxalate, ethylene diamine, 8-hydroxyquinoline and 1,10-phenanthroline. Organophosphines, nitriles, carboxylates and thiols should also ligate well, i.e. exhibit a significant $K_f$, with a palladium electroless metallization catalyst. For example, 3-mercaptopropyltriethoxysilane, 2-(diphenylphosphino)ethyltriethoxysilane, and cyanomethylphenyl trimethoxysilane should serve as suitable catalyst ligating groups in accordance with the invention. Also preferred are ligating groups with antibonding (pi*) orbitals in the ligand, for example aromatic heterocycles such as pyridine and other nitrogen containing aromatics. Such groups give rise to dpi→pi* backbonding interactions that favor complex formation. It has thus been found that a benzyl chloride group provides poor ligating ability whereas an alkylpyridyl provides good ligation to an electroless catalyst.

A variety of compounds may be employed as the electroless catalyst in accordance with the invention, such as palladium, platinum, rhodium, iridium, nickel, copper, silver and gold. Palladium or palladium-containing compounds and compositions generally provide superior catalytic activity and therefore are preferred. Particularly preferred palladium species include bis-(benzonitrile)palladium dichloride, palladium dichloride and $Na_2PdCl_4$. Other salts of $PdCl_4^{2-}$ should also be suitable, such as potassium and tetraethylammonium salts.

The electroless metallization catalysts useful in the processes of the invention are preferably applied to the substrate as a solution, for example as an aqueous solution or a solution of an organic solvent. Suitable organics include dimethylformamide, toluene, tetrahydrofuran, and other solvents in which the metallization catalyst is soluble at effective concentrations.

Means for contacting a substrate with a catalyst solution may vary widely and include immersion of the substrate in a solution as well as a spray application. The catalyst solution contact time required to provide complete metallization of the contact area can vary with catalyst solution composition and age.

A variety of catalyst solutions have been successfully employed, with solutions stabilized against decomposition preferred. Thus, the catalyst solution may comprise ancillary ligands, salts, buffers and other materials to enhance catalyst stability. Though again not wishing to be bound by theory, it is believed many of the catalyst solutions useful in the present invention decompose over time by oligomerization and formation of insoluble oxo-compounds, for example as reported by L. Rasmussen and C. Jorgenson, *Acta. Chem. Scand.*, 22, 2313 (1986). It is believed the presence of catalyst oligomers in the catalyst solution can affect the ability of the catalyst to induce metallization and/or inhibit selectivity of metallization of a patterned substrate. For example, as such catalyst oligomers increase in molecular weight, their solubilities decrease and precipitation of the catalyst can occur.

Suitable agents for stabilizing a catalyst solution can vary with the particular catalyst employed, as is apparent to those skilled in the art. For instance, a metallization catalyst of $PdCl_4^{2-}$ can be stabilized in aqueous solution by addition of excess chloride ion and decreasing pH to inhibit formation of oxo-bridged oligomers of the catalyst, of proposed structures such as $Cl_3PdOPdCl_2(H_2O)^{3-}$, and $Cl_3PdOPdCl_3^{4-}$.

This is supported by the greater stability of catalyst solutions comprising sufficient concentrations of sodium chloride or tetraethylammonium chloride (TEACl) relative to the stability of $PdCl_4^{2-}$ solutions not containing such agents. Such catalyst stabilization can be accomplished by adjustment of chloride ion concentration during preparation of the catalyst solution, or by adjustment of chloride ion concentration after the catalyst solution has attained full catalytic activity. In addition to chloride, other anions that prevent the formation of catalyst oligomers should also be suitable agents for stabilizing a catalyst solution, for example bromide and iodide ions.

Cation effects have also been observed. For example, suitable use of sodium chloride with $Na_2PdCl_4$ provides an active and stablilized catalyst solution. Replacing sodium chloride with ammonium chloride in such a solution, however, results in a solution with little or no activity as a metallization catalyst. In this case, it is believed that the lack of catalytic activity may be the result of the formation of stable cis- or trans-$(NH_3)_2PdCl_2$ species in solution. Replacing sodium chloride with TEACl provides a solution that requires a shorter induction period to reach full activity, and once active remains selective and stable only for a few days. It is further noted that while a number of cations may be suitable, cation selection may be dictated by the specific metallization process. For example, for advanced microelectronic applications, use of sodium ions generally is avoided if possible and, therefore, use of TEACl as a catalyst solution stabilizer may be preferred.

It also has been found that catalyst solutions of higher (less acidic) pH, e.g. pH of greater than 4, can be stabilized with a suitable buffer solution. Preferably, pH of a catalyst solution is controlled by a buffer component which does not appreciably coordinate with the metallization catalyst. For a Pd(II) metallization catalyst, a preferred buffering agent is 2-(N-morpholino)ethane sulfonic acid, referred to herein as MES, available from the Aldrich Chemical Company. This buffer has a $pK_a$ of 6.15 and has been described in Good, et al., *Biochemistry*, 5(2), pp. 467–477 (1966).

Additionally, it has been found that solution preparation methods can affect the stability and metallization activity of a catalyst solution useful in the invention. For example, the catalyst solutions disclosed in Examples 16 and 17 herein are prepared using approximately equivalent initial quantities of acetate buffer, sodium chloride and $Na_2PdCl_4 \times 3H_2O$. In Example 16 herein, an aqueous catalyst solution comprising NaCl and $Na_2PdCl_4 \times 3H_2O$ reaches full activity as a metallization catalyst about 24 hours after preparation at room temperature. Addition of a prescribed amount of acetate buffer to this active solution maintains its catalytic activity. In contrast, preparation of a catalyst solution as described in Example 17 herein by simultaneous mixing of acetate buffer, NaCl and $Na_2PdCl_4 \times 3H_2O$ in aqueous solution yields a catalyst solution which requires about 11 days to reach full activity as a metallization catalyst.

It also has been found that components of a catalyst solution can compete with the catalyst for binding with substrate ligating sites. For example, for 4,4'-(di(carboxylic acid-(N-3-(trimethoxysilyl)propyl)amide))-2,2'bipyridine, the $pK_a$ values of the pyridyl groups are about 4.44 and 2.6, for mono- and di-protonation respectively. See, K. Nakamoto, *J. Phys. Chem.*, 64, 1420 (1960). Thus, in the case of a $PdCl_2$/HCl (aq) catalyst solution, HCl may protonate the pyridyl groups and effectively compete for these sites with the palladium catalyst. While electrostatic interactions may still occur between the metallization catalyst and such a protonated ligating group, coordination type binding will be substantially reduced. It has thus been found that elimination of such ligation competitors from a catalyst solution increases coordination type binding of the catalyst to the substrate ligation functionality.

A wide variety of substrates may be used in accordance with the invention. For example, the substrate may comprise a conductive material such as tungsten or copper, e.g. a copper clad printed circuit board; a semiconductor material such as doped silicon; a dielectric material such as polymeric substrates or ceramic substrates used in electronics applications, and others such as a photoresist coating and glass and quartz substrates. Similarly, a variety of metals may be plated according to the invention including cobalt, nickel, copper, gold, palladium and alloys thereof, and other alloys such as the nickel-iron-boron alloy identified as permalloy. Suitable commercial electroless metallization baths include the nickel electroless plating solution identified as Niposit 468 and sold by the Shipley Company of Newton, Mass.

The processes of the invention are useful for virtually any electroless metallization process, such as electroless plating in printed circuit and printed circuit board manufacture, including metallization of through holes surfaces in double-sided or multilayer printed circuit boards; plating on ceramic materials such as ceramic resistors and ceramic circuit boards; and plating of integrated circuits. More specifically with respect to the metallization of printed circuit board through-holes, the present invention provides in general contacting the nonconductive through-hole walls with a compound or composition comprising electroless catalyst ligating groups. The ligating compound or composition can be admixed with a liquid carrier, and the through-holes surfaces treated with such admixture. After such conditioning, the treated through-holes surfaces are contacted with a suitable electroless catalyst (e.g., the catalyst solution described in Example 12 herein) and then the hole walls metallized according to standard procedures. Electroless nickel or copper plating of through hole walls is common.

The present invention is particularly useful for fabricating circuit lines in electronic printed boards. Electroless plating is an additive process enabling fabrication of high resolution circuit traces with nearly vertical sidewalls. The present invention permits fabrication of high resolution circuit lines without the use of a photoresist patterning sequence. For example, as discussed above, suitable ligating groups or precursors thereof can be selectively modified to provide ligating groups in a selective pattern on a substrate surface. Upon subsequent metallization, a metallized patterned image is provided.

The processes of the invention are also useful to metallize lipid tubule microstructures, which are hollow cylindrical structures composed of up to approximately ten bilayers. Characteristic diameters are between about 0.2 to 0.3 microns and wall thicknesses are between about 5 to 50 nanometers. It is believed the exposed phosphocholine head groups or phosphate groups of the lipid can serve as catalyst ligating groups.

As described in U.S. Pat. No. 4,911,981, incorporated herein by reference, numerous applications for metallized tubules and metallized tubule composite materials are known, including absorbers of electromagnetic radiation, electron emissive surfaces and controlled release reagents. Prior lipid metallization procedures generally require numerous processing steps, resulting in breakage and considerable reduction in aspect ratios from the as-formed tubules to the metal-coated product. Preservation of the tubules aspect ratio during the metallization process is highly desired for many applications of the microstructures. Metallization in accordance with the present invention saves processing time and steps relative to prior systems, and thus can lead to preservation of the aspect ratios of the tubules.

The invention will be better understood by reference to the following examples.

GENERAL COMMENTS

In the following Examples, all contact angle measurements were made with water by the sessile drop method with a water drop and an NRL Zisman-type contact angle goniometer. Ultraviolet absorption data was recorded on a Cary 2400 Spectrophotometer. For measurements of a film on a silica slide, molar absorption coefficients ($\epsilon$) were calculated from measured absorbance values based on a surface concentration of 10M and a film pathlength of $2\times 10^{-7}$ cm. Nitrogen gas used for drying was filtered prior to use by passing through a 0.22 μm filter. All water was deionized.

The following terms when capitalized in the Examples have the following meanings.

"Standard Cleaning Method" means immersing the substrate in a solution of 1:1 v/v concentrated HCl:methanol for 30 minutes. The substrate is water rinsed and immersed in concentrated sulfuric acid for 30 minutes, and then transferred to a container of boiling water and stored therein until use. Immediately prior to use, the clean substrate is removed from the boiling water bath and dried with nitrogen or, alternatively dipped in acetone.

"100% Co Metallization Bath" means a bath prepared as follows. 6.0 g of $COCl_2 6H_2O$, 10.0 g $NH_4Cl$ and 9.8 g ethylenediaminetetraacetic acid disodium salt are dissolved in 150 mL of deionized water and the pH brought to 8.2 by addition of 1M NaOH (aq) solution. Added to three volumes of the Co solution is one volume of a solution consisting of 8.0 g of dimethylamine borane complex in 100 mL of water. "50% Metallization Bath" means a bath prepared by diluting one volume of the 100% Metallization Bath with one volume of water. "25% Metallization Bath" means a bath prepared by diluting one volume of the 100% Metallization Bath with three volumes of water.

"MES Buffer Solution" means a solution prepared as follows. 2.13 g MES×$H_2O$ solid is added to 50 mL water with stirring until dissolution. The pH of the solution is adjusted to 4.9 to 5.0 by dropwise addition of dilute NaOH. The solution is diluted to 100 mL to produce the final buffer. This solution has a MES concentration of 0.1M and is referred to herein as MES Buffer Solution A. MES Buffer Solutions B and C were prepared in a similar manner to MES Buffer Solution A, except that the pH of these solutions are 5.7 and 6.4, respectively.

EXAMPLE 1

This example illustrates application of a ligating layer on a substrate surface by dip coating.

A one-inch square fused silica slide (ESCO Products or Dell Optics) was cleaned by the Standard Cleaning Method. Contact angle of 5° was obtained indicating a clean hydrophilic substrate surface. The slide was dried under nitrogen and placed in a glass holder which permitted exposure of both faces of the slide. The assembly was placed in a beaker containing 250 mL of a toluene solution 1.0 mM in acetic acid and further containing 1% (v/v) β-trimethoxysilylethyl-2-pyridine (available from Huls America—Petrarch Systems). The solution was heated for about 40 minutes until reaching temperature of about 65° C. The solution remained clear and colorless throughout heating. The slide was removed from the solution and rinsed twice in toluene. The slide was then immediately baked for 3 minutes at 120° C. on the surface of a hotplate to complete attachment of the silane compound. After heating, the slide had a contact angle of 45° indicating binding of the more hydrophobic silane compound to the hydrophilic quartz surface. Ultraviolet absorption spectrum of the thus coated slide versus a reference of an uncoated fused silica slide was taken. Absorption maxima were observed at 200 nm and 260 nm with $\epsilon$=4900 $M^{-1}cm^{-1}$ and $3700 M^{-1}cm^{-1}$, respectively. Correspondence between this spectrum and the spectrum of β-trimethoxysilylethyl-2-pyridine in acetonitrile confirmed the binding of the silane compound to the fused silica surface. Calculations based on the relative intensities of the bands of the surface and solution analogs indicate an average surface coverage of approximately one molecular layer of the silane compound.

EXAMPLE 2

This example illustrates application of a ligating film on a substrate surface by spin coating.

A one inch square fused silica slide was cleaned by the Standard Cleaning Method and dried as in Example 1. The slide was placed on the vacuum chuck of a Headway Research Standard Model Spincoater. The top surface of the slide was completely covered with a methanol solution 1.0 mM in acetic acid and further containing 1% (v/v) β-trimethoxysilylethyl-2-pyridine. Excess solution was removed by spinning the slide at 6000 rpm for 30 seconds. The slide was then baked for 3 minutes at 120° C. on the surface of a hotplate. After heating, the slide provided a contact angle of 44°. The ultraviolet absorption spectrum was qualitatively similar to that of the coated slide prepared in Example 1 although the spectral bands were more intense and broader than corresponding bands of the Example 1 spectrum, consistent with bulk film formation in this case.

EXAMPLE 3

This example illustrates stripping of the outer layers of the bulk film to produce a surface film layer of thickness of between one and several molecular layers.

The coated silica slide produced in Example 2 was placed in a glass holder which permitted exposure of both faces of the slide. The assembly was immersed in tetrahydrofuran, and the solution was brought to a boil over 0.5 hour. The slide was removed from the solution, rinsed with room temperature tetrahydrofuran and dried under nitrogen. Ultraviolet absorption spectrum was comparable to the spectrum of the slide prepared in Example 1, indicating removal of the outer layers of the film to produce an ultrathin film on the substrate of thickness of one or several molecules.

EXAMPLE 4

This example illustrates in situ formation of a ligating film precursor with subsequent attachment of the same to a substrate surface.

The ligating precursor was 4,4'-dicarbonyl chloride-2,2'-bipyridine. This compound was prepared by oxidation of 4,4'-dimethyl-2,2'-bipyridine (Aldrich Chemical Co.) with acidic potassium permanganate to 4,4'-dicarboxy-2,2'-bipyridine, as described in A. Sargeson et al., *Aust. J. Chem.*, 39, 1053 (1986), incorporated herein by reference. A flask was charged with 3.5 g (1.39 mM) of this dicarboxy compound and 60 mL toluene (Aldrich Sure Seal), and then 50 mL (68.5 mM) of thionyl chloride (Aldrich Gold Label) was quickly added. The flask was outfitted with a reflux condenser with a CaSO$_4$ drying tube and the mixture refluxed for 6 hours. Virtually all of the initially insoluble material dissolved during reflux to provide a slightly cloudy yellow solution. The solution was cooled to room temperature and filtered through a fritted glass funnel. The filtrate was concentrated under reduced pressure, and the resulting solid repeatedly redissolved in toluene and concentrated under reduced pressure until all traces of thionyl chloride were removed. The resulting yellow solid (3.9 g) was treated with activated charcoal in boiling toluene and filtered. The filtrate was concentrated to about 25 mL. Upon cooling, 4,4'-dicarbonyl chloride-2,2'-bipyridine (2.6 g, 67%) crystallized out of the filtrate as-an off-white solid, mp 142°–144° C. Anal. Calcd for $C_{12}H_6N_2Cl_2O_2$: C, 51.27; H, 2.15; N, 9.97. Found: C, 51.32; H, 2.27; N, 9.54.

A flask contained in a drybox was charged with 0.0703 g (0.25 mM) of 4,4'-dicarbonyl chloride-2,2'-bipyridine and 50 mL of acetonitrile the solution heated to boil to facilitate dissolution. 50 mL of acetonitrile was added and the solution cooled to room temperature. An excess portion (100 μL used; 69 μL, 0.50 mMoles required) of triethylamine (Aldrich Gold Label) (the triethylamine previously dried through a column of Activity I alumina) was added followed by addition of 89 μL (0.50 mM) of 3-(trimethoxysilyl) propylamine (Huls America—Petrarch Systems). Acetonitrile was added to increase the mixture volume to 250 mL and the reaction flask shaken. Ultraviolet absorption spectroscopy of the pale yellow solution confirmed coupling of 4,4'-dicarbonyl chloride-2,2'-bipyridine and 3-(trimethoxysilyl) propylamine to provide 4,4'-(di(carboxylic acid-(N-3-(trimethoxysilyl)propyl)amide))-2,2'-bipyridine, having molecular formula $C_{24}H_{38}O_8N_4Si_2$, the compound referred to herein as "UTF-14B3".

A fused silica slide was cleaned by the Standard Cleaning Method and placed in the pale yellow solution of the UTF-14B3 compound. The solution was heated to 60° C. over a 40 minute period. The slide was then removed, rinsed twice in acetonitrile and baked for 3 minutes at 120° C. on a hotplate. After heating, the coated slide provided a contact angle of about 15°. Ultraviolet absorption spectroscopy confirmed the binding of the UTF-14B3 compound to the slide surface and indicated a film thickness on the slide of between 1 and 2 molecular layers.

EXAMPLE 5

This example illustrates the binding of a palladium electroless metallization catalyst to the UTF-14B3 compound by a sequential addition process.

A 0.002M acetonitrile solution of the UTF-14B3 compound was prepared as in Example 4. Added to this solution was an equal volume of a 0.002M acetonitrile solution of bis(benzonitrile)palladium dichloride. Ultraviolet absorption spectroscopy confirmed the binding of the palladium compound to the UTF-14B3 compound via the observation of new, broad absorption bands at about 220 nm and 327 nm characteristic of the catalyst-ligand complex.

EXAMPLE 6

This example illustrates the binding of a palladium electroless metallization catalyst to the UTF-14B3 compound by a simultaneous addition process.

A flask in a drybox was charged with 4,4'-dicarbonyl chloride-2,2'-bipyridine, 3-(trimethoxysilyl)propylamine, bis(benzonitrile)palladium chloride and triethylamine in a respective concentration ratio of 0.1 mM: 0.2 mM: 0.1 mM: 0.25 mM. 50 mL of acetonitrile was added to dissolve the solid. Acetonitrile was then added to increase the volume of the solution to 100 mL. Ultraviolet absorption spectroscopy of the red-orange solution matched the spectrum of Example 5 confirming formation of the UTF-14B3 compound and the binding thereto of the palladium catalyst.

EXAMPLE 7

This example illustrates metallization of substrate surfaces according to the processes of the invention.

A fused silica slide was coated with the UTF-14B3 compound as in Example 4 and then immersed in a solution of 84 mg of PdCl$_2$ per liter of 0.1M HCl aqueous solution. The solution was gently stirred for 40 minutes and the slide then removed and rinsed twice in water. Ultraviolet absorption spectrum showed strong, broad absorption bands at 220 nm ($\epsilon$=70000 M$^{-1}$cm$^{-1}$) and a weaker band at 327 nm ($\epsilon$=9800 M$^{-1}$cm$^{-1}$) indicating binding of the catalyst. These bands were in agreement with those observed for the UTF-14B3 complex of PdCl$_2$ in acetonitrile (note Examples 5 and 6) and indicate that the surface-bound and solution phase complexes are similar. It was found that greater than 95 percent of the ligating sites of the UTF-14B3 surface had accepted a PdCl$_2$ species. A time dependence study of the uptake of PdCl$_2$ from the catalyst solution by the UTF-14B3 surface film was performed. The absorption intensity at 220 rim, which is proportional to the level of UTF-14B3 bound PdCl$_2$ in the film, was determined as a function of the exposure time of the UTF-14B3 film to the PdCl$_2$/HCl solution. The results showed that about 85% of the ligating sites had accepted the PdCl$_2$ catalyst after 15 minutes exposure of the UTF-14B3 film to the solution.

EXAMPLE 8

This example illustrates the binding rate of the metallization catalyst from solution by the substrate ligating group can be dependent on the nature of the metallization catalyst solution.

A UTF-14B3 coated fused silica slide prepared as in Example 4 was treated with a solution of 11 mg of bis(benzonitrile) palladium dichloride in 100 mL of tetrahydrofuran. Ultraviolet spectrum absorption bands at 220 nm and 327 nm were observed following treatment indicating formation of the UTF-14B3 complex of PdCl$_2$ in the surface film. A time dependence binding study as per Example 7 indicated that binding was greater than 90% complete after a 5 minute treatment of the film with the catalyst solution. The time necessary to achieve a comparable degree of binding using the PdCl$_2$/0.1M HCl (aq) solution of Example 7 was greater than 15 minutes.

EXAMPLE 9

This example illustrates the metallization of a substrate in accordance with the present invention.

A fused silica slide coated with UTF-14B3 as in Example 4 was treated with PdCl$_2$/0.1M HCl (aq) solution for 40 minutes as described in Example 7. The treated slide was water rinsed and placed in 25% Co Metallization Bath with gentle agitation for 4 minutes. Hydrogen gas evolution and metallization of the slide were observed during this time. A thin, homogeneous, mirror-like plate of Co metal was observed over the entire treated area of the slide. The slide was removed from the metallization bath, water rinsed twice and dried under nitrogen. Treatment of a fused silica slide uncoated with UTF-14B3 by the same procedure gave no metallization. Similarly, treatment of a UTF-14B3 coated fused silica slide with the 25% Co Metallization Bath, but without prior treatment with metallization catalyst solution, gave no metallization.

EXAMPLE 10

This example illustrates binding of a metallization catalyst directly to a substrate surface.

An n-type, native oxide silicon wafer (available from Monsanto Co., St. Louis, Mo.) was cleaned by the Standard Cleaning Method and placed in a wafer carrier within a beaker. A fresh 0.001M acetonitrile solution of the UTF-14B3 complex of $PdCl_2$ of Example 6 was added to the beaker, and the solution was allowed to stand at room temperature for 1.5 hours. The wafer was then removed, rinsed twice with fresh acetonitrile and baked for 3 minutes on a hotplate at 120° C. The wafer was then immersed in the 25% Co Metallization Bath for 4 minutes, rinsed twice with water and dried under nitrogen. A Co metal plate was observed over the entire area of the wafer treated with the catalyst solution. Treatment of a clean silicon wafer uncoated with the UTF-14B3 complex of $PdCl_2$ with the 25% Co Metallization Bath did not provide a metal deposit.

EXAMPLE 11

This example illustrates removal of metallization catalyst bound to outer layers of a bulk surface ligating film. Reactivation of the resulting de-catalyzed film with additional metallization catalyst solution permits metallization of the surface.

A fused silica slide coated with a bulk film of β-trimethoxysilylethyl-2-pyridine from Example 3 was treated with $PdCl_2$/0.1M HCl (aq) solution for 15 minutes as described in Example 7. Ultraviolet absorption spectroscopy of the treated slide showed an absorption band at 235 nm in addition to bands at about 200 nm and 260 nm. The 235 nm band is indicative of a surface bound β-trimethoxysilylethyl-2-pyridine complex of $PdCl_2$. The presence of the bands associated with the free surface bound β-trimethoxysilylethyl-2-pyridine indicated that not all ligation sites within the film had complexed $PdCl_2$. The fused silica slide was then immersed in heated tetrahydrofuran as described in Example 3. After removal of the slide from the tetrahydrofuran bath, ultraviolet absorption showed an absence of the surface bound $PdCl_2$ as evidenced by the disappearance of the 235 nm band. Failure of an identically treated slide to metallize upon immersion in the 25% Co Metallization Bath confirmed the absence of metallization catalyst on the surface. The remaining absorption bands at 200 nm and 260 nm were consistent in intensity and position with those observed for ligation films of approximate monomolecular average thickness described in Example 1. Subsequent treatment of this slide with fresh metallization catalyst solution restored the 235 nm absorption band to the spectrum and, upon immersion of the slide in the 25% Co Metallization Bath, Co metal deposited on the slide.

EXAMPLES 12–18

These examples illustrate control of catalytic activity and stability of a metallization catalyst through formulation of catalyst solutions comprising specific additives. Each solution of the examples was tested for metallization selectivity as follows. An n-type, native oxide silicon wafer was dip coated with β-trimethoxysilylethyl-2-pyridine. This wafer and a second uncoated n-type, native oxide silicon wafer were each treated with the described catalyst solution for 15 minutes and water rinsed twice. Each wafer was then immersed in the 25% Co Metallization Bath for 4 minutes, water rinsed twice and dried under nitrogen. Each wafer was then examined for evidence and quality of metallization. Plating is considered selective if the coated wafer was metallized but no metallization of the uncoated wafer was observed. Plating is considered non-selective if both wafers metallize.

EXAMPLE 12

An electroless metallization catalyst solution preferred for its stability and catalytic activity and selectivity, was prepared as follows: a vessel was charged with 11 mg of $Na_2PdCl_4 \times 3H_2O$ in 1 mL of 1.0M NaCl (aq) and water added to bring the volume of the mixture to 100 mL. The resulting clear green-yellow solution was initially inactive as a metallization catalyst. After standing at room temperature for 24 hours, the solution turned a deeper yellow color and exhibited high activity and selectivity as a Co metallization catalyst. Both catalyst activity and selectivity of the solution were maintained for more than 30 days without further treatment.

EXAMPLE 13

A solution was prepared by dissolving 8.6 mg. of $Na_2PdCl_4 \times 3H_2O$ in 100 mL water. Immediately after preparation, this solution exhibited selective Co metallization. However, the solution was unstable and decomposed within hours via precipitation of palladium-containing oligomers.

EXAMPLE 14

A solution was prepared by adding 10 mL of an aqueous 0.1M tetraethylammonium chloride solution to 11 mg of $Na_2PdCl_4 \times 3H_2O$ in a 100 mL volumetric flask and diluting to the mark with water. The clear, yellow solution had pH 4.5 and was an active and selective Co metallization catalyst within one hour of preparation. Within 24 hours of preparation, this solution acquired a dull, dirty yellow color and visually exhibited evidence of faint particulate matter. The solution pH was approximately 4.2 at this time. The solution filtered through 0.22 μm cellulose filters as well as unfiltered solution gave selective metallization. After 48 hours from preparation, the solution contained a solid precipitate and was unusable as a metallization catalyst.

EXAMPLE 15

An aqueous acetate buffer solution was prepared which was 0.5M initially in both sodium acetate and acetic acid. 2 mL of this solution was added to 11 mg of $Na_2PdCl_4 \times 3H_2O$ in a 100 mL volumetric flask and the flask diluted to the mark with water. The solution was clear, green-yellow in color with pH 4.6 and was initially inactive as a metallization catalyst. Within 24 hours of preparation, the solution yellowed and became an active, though nonselective, metallization catalyst. Filtering as described for the solution of Example 14 did not affect the behavior of the solution. Solution pH remained stable (in the range of 4.6 to 4.7) for at least 2 days following preparation.

EXAMPLE 16

100 mL of the active catalyst solution of Example 12 was prepared, and 2 mL of the solution was removed and replaced with a 2 mL aliquot of a 0.5M acetate aqueous buffer which was 0.5M in both sodium acetate and acetic acid. The resulting clear, yellow solution had pH 4.55 and was an active, selective Co metallization catalyst. The solution remained an active, selective metallization catalyst for at least 2 days following its preparation, at which time it was yellow in color with pH 4.5.

EXAMPLE 17

A solution was prepared by simultaneous addition of 1 mL of NaCl (aq) solution and 2 mL of 0.5M acetate aqueous buffer solution (the buffer solution 0.5M in both sodium acetate and acetic acid) to 11 mg solid $Na_2PdCl_4 \times 3H_2O$ in a 100 mL volumetric flask. Following dissolution of the solid, the flask was diluted to the mark with water. The clear, green-yellow solution had pH 4.7. Although the pH remained stable at this value for at least 7 days, the solution exhibited no activity as a metallization catalyst during this time. The activity of the solution as a metallization catalyst increased slowly during the following 3 to 4 days. Approximately 11 days after preparation, the solution reached full activity as a selective Co metallization catalyst.

EXAMPLE 18

A solution was prepared by dissolving 11 mg of $Na_2PdCl_4 \times 3H_2O$ in 10 mL of 0.01M $NH_4Cl$ (aq) solution. The clear, green-yellow solution was inactive as a metallization catalyst for at least 2 days following preparation. A drop in pH from 3.8 to 3.5 occurred during this time.

EXAMPLE 19

This example illustrates that a substrate requires a suitable ligating group for the substrate to be metallized in accordance with the present invention.

Three n-type, native oxide silicon wafers were cleaned by the Standard Cleaning Method. The first wafer was dip coated with ε-trimethoxysilylethyl-2-pyridine as in Example 1. The second wafer was coated with a film of 4-chloromethylphenyltrimethoxysilane using the surface silanization procedure described in Example 1. Contact angles of 45° (first wafer) and 70° (second wafer) were obtained indicative of coating of the wafer surfaces. The third wafer was not coated and provided a contact angle of approximately 5°.

Each of the wafers was immersed in the active catalyst solution of Example 12 for 15 minutes, water rinsed and then immersed in the 25% Co Metallization Bath for 4 minutes. The wafers were removed from the Co bath, water rinsed and dried under nitrogen. A full, homogeneous, mirror-like plate of Co metal was observed on the β-trimethoxysilylethyl-2-pyridine coated wafer in areas treated with the catalyst solution. No Co metal plate was observed on either of the other wafers.

EXAMPLE 20

This example illustrates selective electroless metallization according to the present invention.

Two n-type, thermal oxide (350 angstrom oxide thickness) silicon wafers were cleaned by the Standard Cleaning Method and coated with β-trimethoxysilylethyl-2-pyridine as in Example 1. Film integrities were confirmed by contact angle measurements. The wafers were patterned with a serpentine mask using ultraviolet exposure with Karl Suss Model MJB 3 Contact Printer equipped with Karl Suss Model 507X Xenon Lamp (254 nm). LrV power level was 6.0 mW/cm$^2$ at 254 nm and exposure time was 15 minutes. The first wafer was treated with the active catalyst solution of Example 12, and metallized by immersing the wafer in the 25% Co Metallization Bath for 4 minutes. The second wafer was treated with the Pd/Sn colloidal catalyst identified as Cataposit 44 (Shipley Company, Newton, Mass.) and metallized with cobalt by standard procedures. Each wafer was examined under an optical reflection microscope. For the wafer treated with the solution of Example 12, the completeness of metallization in the plated regions and the lack of debris in the clear fields were superior compared to the same characteristics of the wafer metallized with the Cataposit 44 catalyst.

EXAMPLE 21

This example illustrates the ability to control the adhesion of a metal plate to an underlying substrate by variation of the chemical bond strength between the metallization catalyst and surface ligating groups.

Two n-type, native oxide silicon wafers were cleaned by the Standard Cleaning Method. The first wafer was dip coated with the β-trimethoxysilylethyl-2-pyridine solution as described in Example 1. The second wafer was treated by the UTF-14B3 compound as described in Example 4. Each wafer was treated for 15 minutes with the active catalyst solution of Example 12, water rinsed twice, and immersed in the 25% Co Metallization Bath for 4 minutes. The wafers were removed from the bath, water rinsed and dried under nitrogen. Complete, homogeneous, mirror-like plating of Co metal was observed on each wafer where exposed to the catalyst solution. Measurement by Dektak profilometry showed plating on each wafer of equal thickness (350±50 angstroms). A piece of Scotch™ brand adhesive tape was placed on the plated areas of each wafer. The tape was removed from each wafer in a slow steady manner. Tape removal lifted between about 50–70% of the Co metal film as flakes from the wafer treated with the β-trimethoxysilylethyl-2-pyridine compound. No Co metal was removed from the second wafer coated with the UTF-14B3 compound after numerous applications and removals of tape.

EXAMPLE 22

This example illustrates the ability to deposit thick films of highly stressed materials by the processes of the invention.

The procedure of Example 21 was repeated, except immersion of the wafers in the 25% Co Metallization Bath was increased from 4 minutes to 50 minutes. Severe and nearly total flaking of the Co plate on the β-trimethoxysilylethyl-2-pyridine coated wafer was observed after about 5 to 10 minutes in the metallization bath. A homogeneous, adherent, mirror-like Co metal plate was observed on the UTF-14B3 coated wafer even after 50 minutes in the Co bath. Dektak profilometry showed a metal thickness of 2750±250 angstroms for this second wafer. Application and removal of Scotch™ brand tape as in Example 21 did not remove Co from the second wafer.

EXAMPLE 23

This example illustrates modification of a tungsten metal surface by the method of the invention.

Three CVD tungsten on silicon wafers were cleaned by immersion in a 30% $H_2O_2$ (aq) solution for 1 hour and then water rinsed. The first wafer was dip coated with β-trimethoxysilylethyl-2-pyridine as in Example 1 and the second wafer was coated with UTF-14B3 as in Example 4. The third wafer was not coated and used as a control. Each wafer was immersed in the Catalyst Solution 2 as prepared in Example 28 herein for 15.minutes, water rinsed and then immersed for four minutes in the 25% Co Metallization Bath. Each wafer was then water rinsed and dried under nitrogen. Homogeneous Co plates were observed for the first and second coated Co tungsten wafers, but no metallization was observed for the third control wafer. Scotch™ tape adhesion tests as described in Example 21 showed greater metal adhesion for the UTF-14B3 coated wafer than for the β-trimethoxysilylethyl-2-pyridine coated wafer.

EXAMPLE 24

This example illustrates the ability to plate surfaces with nickel by the method of the invention.

A thermal oxide $SiO_2$ wafer was dip coated with β-trimethoxysilylethyl-2-pyridine as in Example 1. The coated wafer was treated with Catalyst Solution 2 (as prepared in Example 28 herein) for 0.5 hours. The wafer was water rinsed and then immersed for 20 minutes in the nickel electroless metallization solution identified as Niposit 468 (Shipley Company). This nickel metallization solution was heated to 25° C. and formulated according to manufacturer's instruction and diluted to 5% strength. A homogeneous nickel deposit was obtained over the entire area of wafer contacted by the catalyst solution. A clean thermal oxide $SiO_2$ wafer that was not coated with the β-trimethoxysilylethyl-2-pyridine was subjected to the above procedures but nickel did not deposit on the uncoated wafer.

EXAMPLE 25

This example illustrates distributing ligating moieties throughout a substrate according to the present invention.

A poly(4-vinylphenol) (PVP, average molecular weight= 5000 g/mol) stock solution was prepared by sonicating a mixture of 26 g of PVP and 74 g of diglyme. 125 mg of 4,4'-dimethyl-2,2'-bipyridine were dissolved in 10 mL of the PVP stock solution. A film of this solution was spin coated at 4000 rpm for 30 seconds onto a clean, n-type native oxide silicon wafer. A control was prepared by spin coating by identical procedure the PVP stock solution onto a clean, n-type native oxide silicon wafer. The two coated wafers were baked at 90° C. for 0.5 hours. Each coated wafer was treated with the active catalyst solution of Example 12 for 60 minutes, water rinsed twice and immersed in the 25% Co Metallization Bath for 4 minutes with agitation. The wafers were then water rinsed and dried under nitrogen. A complete, homogeneous, plate of Co was observed on the wafer coated with the bipyridine solution in regions contacted with the catalyst solution. No metallization of the control wafer was observed.

EXAMPLE 26

This example illustrates metallization of a material which inherently contains ligating moieties.

Two 100 mg samples of neutral alumina (Fisher Scientific; 80–200 mesh powder; Brockman activity I) were placed in separate vessels. The samples were each equilibrated in water by washing thoroughly with three 50 mL portions of water. The first sample was maintained under water as a control and the second sample treated for 15 minutes with the active catalyst solution of Example 12, with occasional stirring. Each sample was decanted and washed separately with 6 portions of water and then dried for 2 minutes on a suction funnel after the final wash. The 100% Co Metallization Bath was then added to each sample and the resulting slurries stirred for 60 minutes. For the sample treated with the active catalyst solution of Example 12, vigorous $H_2$ evolution was observed during stirring, and the resulting gray-black Co metallized alumina particles were magnetic. No evidence of metallization of the control sample was observed.

EXAMPLE 27

This example illustrates metallization of ceramic material according to the processes of the invention.

The Nextel fibers (3M Corp.) employed in this example were ceramic composite fibers composed of alumina, boria and silica coated with a polymeric substance. Metallized samples of these fibers have numerous applications, including as absorbers of electromagnetic radiation.

Three one inch strands of Nextel Roving 312, Type 1800D Ceramic Fibers were employed. The first strand was used without further treatment. The second strand was flame cleaned to remove the polymeric surface coating. The third strand was cleaned by the Standard Cleaning Method. Each strand was water rinsed twice and immersed in the active catalyst solution of Example 12 for 15 minutes. The strands were removed from the solution and repeatedly water rinsed to remove the catalyst solution. The strands were then metallized using the 50% Co Metallization Bath. In each case, hydrogen evolution and fiber darkening indicated metallization of each of the fibers was observed within the first two minutes of exposure to the Co bath. Metallization of the first strand is stopped after 7 minutes by quenching with water. The metallic gray fibers were dried under nitrogen and shown to be magnetic by their attraction to a permanent magnet. Metallization of the second and third strands was allowed to proceed for 60 minutes prior to quenching. In each case, the magnetic, metallic gray fibers were obtained. Some flaking of the Co metal from the flame cleaned strand was noticed during the aqueous wash of those fibers following metallization. No flaking of Co metal from the third strand (Standard Cleaning Method) was observed. Repetition of these procedures using strands which had not been treated with the active catalyst solution of Example 12 gave no Co metallization. No Co metallization was observed upon repetition of the procedure using ceramic fibers not treated with the catalyst solution.

EXAMPLE 28

This example illustrates preparation of metallization catalyst solutions in accordance with the invention-at pH values greater than 4, and stabilization of the solutions by control of chloride ion concentrations.

Three catalyst solutions were prepared as follows. Into each of three 100 mL volumetric flasks was added 11.3 mg $Na_2PdCl_4 3H_2O$. A 1 mL aliquot of 1M NaCl (aq) solution was added to the first two flasks, which were designated as Solutions 1. and 2 respectively. A 2 mL aliquot of 1M NaCl (aq) solution was added to the third flask, which was designated as Solution 3. After dissolution of solids, a 10 mL aliquot of the MES Solution A having pH of 4.9 was added to each of the three solutions, and each flask was diluted with water to a volume of 100 mL. Three silicon wafers were dip coated with β-trimethoxysilylethyl-2-pyridine as in Example 1 and were each treated with one of the catalyst Solutions 1, 2 and 3, rinsed twice with water, and then immersed in the 25% Co Metallization Bath for 4 minutes. None of the wafers were metallized.

After allowing the three catalyst solutions to stand overnight, three silicon wafers dip coated with β-trimethoxysilylethyl-2-pyridine were again each treated with one of catalyst Solutions 1, 2 and 3, rinsed twice with water, and immersed in the 25% Co Metallization Bath for 4 minutes. Full metallization was observed for the wafers treated with Solutions 1 and 2. No metallization was observed for the wafer treated with Solution 3. Uncoated silicon wafers that were treated with Solutions 1, 2 and 3 also did not metallize.

A 10 mL aliquot of Solution 2 was then removed and replaced with a 10 mL aliquot of 1.0M NaCl (aq) solution. The approximate compositions expressed in terms of initial components of the solutions are shown in the Table below:

| Solution | [Cl$^-$] | pH | [MES] | mg Pd/0.1 L |
|---|---|---|---|---|
| 1 | 0.01 $\underline{M}$ | 4.84 | 0.01 $\underline{M}$ | 11.3 |
| 2 | 0.099$\underline{M}$ | 4.84 | 0.009$\underline{M}$ | 10.3 |
| 3 | 0.02 $\underline{M}$ | 4.88 | 0.01 $\underline{M}$ | 11.3 |

The concentrations of total MES and Pd$^{2+}$ in the solutions are equivalent to within 10%. The principal differences involve total chloride ion concentrations. The pH of solutions 1–3 remain in the range of 4.65 to 4.90 during the lifetime of these experiments.

Catalytic activity of each solution was monitored daily via treatment of β-trimethoxysilylethyl-2-pyridine coated and uncoated Si wafers with each solution followed by metallization with the 25% Co Metallization Bath. Solution 1 served as a control. It exhibited selective metallization of coated Si wafers for about 7 days following preparation. Thereafter, the solution loses its ability to catalyze metallization of wafer surfaces and eventually produced a brown precipitate. Solution 2 (as modified) continued as an active, selective metallization catalyst for about 1 month and no precipitation was observed. Addition of a large chloride ion aliquot to catalytically active Solution 1 can therefore provide at least a four-fold increase in solution stability. Solution 3 slowly increased in catalytic activity with time and full activity was reached about 4 to 5 days after solution preparation. The solution remained an active, selective metallization catalyst for at least one month after preparation. In this case, a two-fold increase in chloride ion concentration at the time of solution preparation can also prolong the useful life of the catalyst solution. However, addition of more Cl$^-$ at the time of solution preparation also increases the time to reach full activity. Stable catalyst solutions can be prepared at pHs significantly greater than pH of 4 using these methods. For example, catalyst solutions stable at pH of about 5.7 or 6.4 can be prepared following the method described for Solution 2 above using MES Buffer Solutions B or C, respectively, in place of MES Buffer Solution A.

EXAMPLE 29

This example illustrates control of the minimum contact time between a metallization catalyst solution and substrate necessary to provide complete substrate metallization. Control is achieved by adjustment of catalyst composition and age.

"Minimum solution contact time" is defined for this example as the time necessary for a catalyst solution to contact a β-trimethoxysilylethyl-2-pyridine coated wafer to yield full and selective metallization on the wafer following a water rinse and subsequent 4 minute treatment with the 25% Co Metallization Bath.

A variety of catalyst solutions were prepared as described in the Table below. The composition represented by Solution 1 in the Table is identical to that described in Example 12. Solutions 2 and 3 were prepared using MES Buffer Solutions B and C, respectively, by following the procedures described in Example 28. Solution 4 represents a more aged version of Solution 3. Solution age (Soln. Age) was measured from initial catalyst dissolution at solution preparation.

| Soln | [Cl$^-$] | [MES] | mg Pd/0.1L | Soln. Age | pH | Min. Time |
|---|---|---|---|---|---|---|
| 1 | 0.01 $\underline{M}$ | 0 | 11.3 | 10 days | 3.7 | ≧10 min. |
| 2 | 0.118$\underline{M}$ | 0.009 $\underline{M}$ | 10.3 | 2 days | 6.3 | 1 min. |
| 3 | 0.11 $\underline{M}$ | 0.009 $\underline{M}$ | 10.3 | 2 days | 5.7 | 3 min. |
| 4 | 0.11 $\underline{M}$ | 0.009 $\underline{M}$ | 10.3 | 30 days | 5.7 | 2 min. |

As shown in the above Table, control of the minimum contact time can be achieved by variations in the catalyst solution composition and age. For Solution 1 aged 10 days, minimum solution contact time was greater than or equal to 10 minutes. For Solution 2 aged 2 days, minimum solution contact time was 1 minute. For Solution 3 aged 2 days, minimum solution contact time was 3 minutes. For Solution 4 aged 30 days, minimum solution contact time was 2 minutes.

EXAMPLE 30

This example illustrates chemical modification of a substrate surface to provide functional groups capable of ligating an electroless metallization catalyst.

A one inch square, 2 mm thick piece of high-density polyethylene with contact angle of 83° was placed for 1.5 hours in a 70° C. acidic dichromate solution consisting of 9.2 g of $K_2Cr_2O_7$ and 80 mL of concentrated $H_2SO_4$ in 46 mL of water. The solution was then cooled to room temperature over 1.5 hours, and the polymer removed and sequentially washed with 5 portions water, 2 portions acetone and 2 portions toluene. After washing, the polymer had a contact angle of 63° C. The polymer was immersed for 20 minutes in a saturated solution of bis (benzonitrile) palladium dichloride in toluene, and then rinsed with toluene and dried under nitrogen. The sample was then immersed in the 50% Co Metallization Bath for 4 minutes, rinsed twice with water and dried under nitrogen. A mirror-like, adherent plate of Co metal was deposited over the entire area treated with the catalyst solution. A second one inch square, 2 mm thick piece of high-density polyethylene was subjected to the same procedure, except the second polymer square was not contacted with the dichromate bath. No metallization of the second square was observed.

EXAMPLE 31

This example illustrates metallization of a polymer substrate by binding a ligating film to the polymer surface according to the present invention.

Two one inch square, 2 mm thick pieces of polyethersulfone (contact angle 53°) were oxidized in a dichromate bath as described in Example 30. Following successive rinses of the samples with 5 portions of water, 2 portions of acetone and 2 portions of toluene (contact angle now 64°), the samples were dried under nitrogen and one sample was exposed to the active catalyst solution of Example 12 for 15 minutes. Metallization of the thus treated polyethersulfone was attempted as described in Example 30 for polyethylene. No metallization of the polyethersulfone oxidized surface occurred indicating that dichromate oxidation did not generate functional groups capable of ligating with the metallization catalyst. The second piece of oxidized polyethersulfone was dip coated with β-trimethoxysilylethyl-2-pyridine. This second polyethersulfone sample has a contact angle of about 50° after coating. Treatment of this second polyethersulfone sample with the active catalyst solution of Example 12, and the 25% Co Metallization Bath as described above provided a Co plate on that portion of the surface contacted by the metallization catalyst solution. The Co metal plate was dull and gray in color but was full and homogeneous. Treatment of a polyethersulfone sample which had not been oxidized with dichromate or coated with the ligating film gave no metallization.

EXAMPLE 32

This example illustrates the construction of a metallizable film on a substrate surface by sequential addition of surface adsorbent component, ligating component and metallization catalyst to the surface.

A clean fused silica slide was coated with a methanol solution 1.0 mM in acetic acid and containing 1% (v/v) 3-(trimethoxysilyl)propylamine (referred to herein as UTF-14) by dip coating. The coated slide had a contact angle of about 30°. Ultraviolet absorption spectrum showed a weak peak at 200 nm indicative of the chemisorbed silyl propylamine compound. A solution containing 100 mg of 8-quinoline sulfonic acid chloride (referred to herein as UTF-QS) and 300 μL of triethylamine (the triethylamine previously dried through a column 0f Activity I alumina) in 20 mL of acetonitrile was added to a Coplin jar containing the coated slide. The orange solution was occasionally mixed, and after 1 hour, the slide was removed and rinsed with acetonitrile and dried under nitrogen. The dried slide had a contact angle of about 56°. Ultraviolet absorption spectrum showed bands at about 215 nm and 280 nm. These bands were consistent with those observed for the UTF-14QS compound in acetonitrile solution ($\lambda=214$ nm, $\epsilon=45500 M^{-1}cm^{-1}$; $\lambda=276$ nm, $\epsilon=6000 M^{-1}cm^{-1}$) confirming the binding of the quinoline sulfonic acid chloride to the silyl propylamine coated surface. The value of $\epsilon=6000 M^{-1}cm^{-1}$ obtained at 215 nm for the coated surface suggested greater than 20 percent surface coverage of the UTF-14QS compound.

The slide coated with the UTF-14QS compound was then immersed in the active catalyst solution of Example 12 for 0.5 hour, water rinsed and dried under nitrogen. Ultraviolet absorption spectrum of the thus treated slide was indicative of binding of the catalyst, showing a strong absorption at 210 nm ($\epsilon=32000 M^{-1}cm^{-1}$) and broad shoulder at about 290 nm ($\epsilon=13000 M^{-1}cm^{-1}$). Catalyst ligation was confirmed by treatment of the slide with the 25% Co Metallization Bath for 4 minutes. A smooth, full, mirror-like Co plate was obtained over the entire surface of the slide treated with the catalyst solution. A similarly prepared slide coated with the UTF-14QS compound, but which had not been exposed to a metallization catalyst, was not metallized upon treatment with the Co solution.

EXAMPLE 33

This example illustrates the ability to metallize substrates modified with a chelating group comprising the ethylene diamine function by the method of the invention.

Glass microscope slides were cleaned via the Standard Cleaning Method. N-2-aminoethyl-3-aminopropyltrimethoxysilane, of formula $(CH_3O)_3SiCH_2CH_2CH_2NHCH_2CH_2NH_2$ (referred to herein as UTF-EDA), was used as received from Huls of America (Bristol, Pa.) and was used as the surface coating applied to the slides. The clean glass slides were treated by immersion for 15 minutes at room temperature in a solution consisting of 250 mL of freshly mixed 94% vol. acidic, anhydrous methanol (Aldrich Sure-Seal containing 1.0 mM acetic acid), 5% vol. water, and 1% vol. UTF-EDA. The slides were removed from the treatment solution, rinsed twice in methanol and baked for 5 minutes at 120° C. on the surface of a hotplate to remove residual solvent. Contact angles were about 17° for the freshly prepared slides. The contact angles slowly increased with time and reached stable values of about 30° within 12 hours after sample preparation.

A clean, blank slide uncoated by UTF-EDA serving as a control and a UTF-EDA coated slide as prepared above were each treated for 30 minutes with the metallization catalyst described as Solution 1 of Example 28. The age of the catalyst solution was 3 days and its pH was 4.9. Each of the slides was then rinsed three times with water and immersed in a 25% Co Metallization Bath for 7 minutes. A homogeneous, mirror-like Co metal plate was observed over the entire region of the UTF-EDA coated slide treated by Solution 1. A complete absence of metallization on the control slide indicated that the metallization of the UTF-EDA coated slide was selective. Application of the Scotch™ tape adhesion test to the Co metal plate resulted in complete adherence of Co metal to the slide. This indicates that UTF-EDA films catalyzed and metallized by the method of the invention exhibit superior adhesion of Co metal films compared to the β-trimethoxysilylethyl-2-pyridine films described in Example 21.

EXAMPLE 34

This example illustrates the ability to use organotitanate materials to provide the adhesive functions in preparing a surface which is metallizable by the method of the invention.

The adhesive/chelating agent 2-propanolato-tris (3,6-diaza)-hexanolato-titanium (IV), of chemical formula $HC(CH_3)_2OTi[O(CH_2)_2NH(CH_2)_2NH_2]_3$ (referred to herein as UTF-44) was used as received from Kenrich Petrochemicals, Inc. (Bayonne, N.J.). A surface treatment solution was prepared by dissolving 3.7 g of UTF-44 in a 250 mL volumetric flask containing 100 mL of 2-propanol and diluting to the mark with 2-propanol. Native oxide n-type silicon wafers were cleaned by the Standard Cleaning Method and immersed in this solution. The solution containing the wafers was placed on a hotplate and brought to 60° C. over the course of 60 minutes. The solution remained clear during this time. The treated wafers were removed, rinsed twice in 2-propanol, dried under nitrogen, and baked for 3 minutes at 120° C. on a hotplate. Contact angles of 16° were obtained on the freshly prepared wafers. Contact angles slowly increased with time and reached a value of 22° approximately 16 hours after baking of the wafers.

One of the UTF-44 coated wafers so prepared was treated for 60 minutes with a saturated solution of bis(benzonitrile)palladium(II) dichloride in toluene. The wafer was rinsed twice in toluene and dried under nitrogen. A clean, blank wafer uncoated by UTF-44 was subjected to identical treatment and served as a control. Both wafers were immersed in a 25% Co metallization bath for 4 minutes, rinsed twice in distilled water and dried under nitrogen. Selective metallization of the UTF-44 coated wafer was observed as a homogeneous, mirror-like Co metal plate over the area of the wafer contacted by the bis(benzonitrile)palladium(II) dichloride/toluene solution.

EXAMPLE 35

This example illustrates the ability to catalyze the UTF-44 film of Example 34 towards Co metallization using an aqueous-based catalyst solution.

A UTF-44 coated wafer prepared as described in Example 34 and a clean, blank control wafer uncoated with UTF-44 were treated with catalyst Solution 1 from Example 28 for 60 minutes. The wafers were rinsed twice in distilled water and then immersed in 25% Co metallization bath for 7 minutes. The UTF-44 coated wafer metallized as a homogeneous, mirror-like Co metal plate over the region contacted by Solution 1. A Scotch™ tape adhesion test applied to the metal film following aqueous rinse and drying under nitrogen gave complete adhesion of the metal to the substrate, a result identical to that described in Example 33.

EXAMPLE 36

This example illustrates the ability to metallize lipid tubule microstructures through the process of the invention.

The tubules used in this example were grown using 1,2-bis-(10,12-tricosadiynoyl)-sn-glycero-3-phosphorylcholine lipid ($DC_{23}PC$; JP Laboratories, Inc., Piscataway, N.J.) and the homogeneous crystallization technique from ethanol/water as disclosed in U.S. Pat. No. 4,911,981, incorporated herein by reference. The tubules were dialyzed with water prior to use.

A tubule suspension in water was gravity filtered to remove excess water. The moist white tubules were placed in a beaker and 15 mL of the active catalyst solution of Example 12 added with gentle mixing to disperse the tubules. The mixture was allowed to stand for 1.5 hours with occasional swirling to maintain suspension of the tubules. The mixture was then gravity filtered and the tubules gently and thoroughly water washed until the draining wash water was colorless. The resulting yellow-beige tubules were then suspended in 20 mL of water and 20 mL of the 50% Co Metallization Bath added and the mixture swirled. Metallization was to allowed to proceed for 25 minutes without additional mixing during which time evolution of $H_2$ was observed. The metallization solution was carefully withdrawn by pipette and the metallized tubules washed to the bottom of the vessel with water. No agglomeration of the tubules was observed after standing in water overnight. The gray-black Co plated tubules were magnetic. Microscopic examination (403× magnification) indicated a range in the amount of metallization over the surface area of the tubules. A control batch of tubules that was not treated with a metallization catalyst did not metallize upon exposure to the Co metallization solution.

The foregoing description of the present invention is merely illustrative thereof, and it is understood that variations and modifications can be made without departing from the spirit or scope of the invention as set forth in the following claims.

We claim:

1. An article of manufacture comprising an electroless metal deposit in an image pattern on a substrate, said substrate, at least where coated with said metal deposit, having bonded to its surface one or more multidentate chemical groups ligated by coordination bonding other than by electrostatic interaction with a substantially tin-free, electroless metallization catalyst.

2. The article of claim 1 where the multidentate chemical groups comprise one or more moieties selected from the group consisting of aromatic heterocycle, amino, phosphino, carboxylate and nitrile.

3. The article of claim 1 where the substrate chemical groups comprise one or more moieties selected from the group of pyridyl and ethylene diamine.

4. The article of claim 1 where the electroless metallization catalyst is a palladium catalyst.

5. The article of claim 4 where the catalyst is selected from the group consisting of bis(benzonitrile) palladium dichloride, palladium dichloride and salts of $PdCl_4^{2-}$.

* * * * *